United States Patent [19]

Freitag et al.

[11] Patent Number: 4,520,812
[45] Date of Patent: Jun. 4, 1985

[54] METHOD AND APPARATUS FOR CONTROLLING A PRESSURE LEVEL IN A RESPIRATOR

[75] Inventors: Lutz Freitag; Michael Wendt; Franz J. Dankwart, all of Münster, Fed. Rep. of Germany

[73] Assignee: Drägerwerk AG, Fed. Rep. of Germany

[21] Appl. No.: 479,145

[22] Filed: Mar. 28, 1983

[30] Foreign Application Priority Data

Apr. 1, 1982 [DE] Fed. Rep. of Germany ....... 3212097

[51] Int. Cl.³ ............................................. A61M 16/00
[52] U.S. Cl. ........................... 128/204.25; 128/207.14
[58] Field of Search ...................... 128/204.25, 204.18, 128/205.19, 207.14, 207.15, 207.16, 204.21, 204.23, 910, 204.24, 205.24, 204.26

[56] References Cited

U.S. PATENT DOCUMENTS

| | | | |
|---|---|---|---|
| 3,485,243 | 12/1969 | Bird et al. | 128/204.25 |
| 3,556,097 | 1/1971 | Wallace | 128/203.28 |
| 3,993,059 | 11/1976 | Sjostrand | 128/205.13 |
| 4,030,492 | 6/1977 | Simbruner | 128/200.21 |
| 4,265,237 | 5/1981 | Schwanbom et al. | 128/204.25 |
| 4,270,530 | 6/1981 | Baum et al. | 128/204.25 |

FOREIGN PATENT DOCUMENTS 2063686  6/1981  United Kingdom ........... 128/204.25

*Primary Examiner*—Henry J. Recla
*Attorney, Agent, or Firm*—McGlew and Tuttle

[57] ABSTRACT

A method of and apparatus for producing a controlled pressure level in a respirator for human patients which is equipped with a tracheal tube 3 connected to the respirator and connectable to the trachea, comprises producing an oscillatory gas stream by means of two opposite gas jets in an attachment tube 4 which has two end openings. By controlling the pressure and/or frequency of the gas jets, a varying pressure level propagating into the tracheal tube is modulated onto the gas stream. The respirator for carrying out the method comprises two gas jet pipes 20, 21 having nozzle tips 24, 25 of which one discharges or points within the attachment tube 4 substantially in the direction of the tracheal tube 3 and the other substantially in the opposite direction.

14 Claims, 6 Drawing Figures

METHOD AND APPARATUS FOR CONTROLLING A PRESSURE LEVEL IN A RESPIRATOR

FIELD AND BACKGROUND OF THE INVENTION

This invention relates in general to repirators and in particular to a new and useful apparatus for connecting a respirator through a tracheal tube to a person's trachea for regulating the flow of gases therethrough and to a method of producing a control pressure level in a respirator for human patients which is equipped with a tracheal tube connection to the respirator.

For about the last ten years, respirators have been known which operate with so called high frequency jet ventilation (HFJV). Developed embodiments of such apparatus were demonstrated at the Central-European Congress of Anesthesiologists, Berlin, Septemeber, 1981. In a new version, the frequency range has been extended to 1,200 breath pulses per minute. The HFJV technique is beneficial primarily to patients with barotraumas and bronchial fistulas. An imposed high frequency respiration is advantageous particularly in the aftermath of any substantial lowering of the pressure in the lungs. It also facilitates the work of the heart. The total ventilation of many patients can thereby definitely be improved. By adjusting a proper air pulse, modulated respiratory curves may be obtained, corresponding to so called Engstroöm pressure curves. In practice, however, the pressure modulation curve cannot be extended to obtain a negative pressure in the trachea. It is further disadvantageous that the steepness of the pressure variation edges (dP/dt) cannot be augmented to satisfy the therapy requirements.

The problem imposed is therefore to improve the known method of producing a controllable pressure, to the effect of augmenting the amplitude of the pressure modulation, providing means for varying the amplitude faster, and extending thereby the general applicability of the method to the treatment of further pathological symptoms.

SUMMARY OF THE INVENTION

In accordance with the invention a method of producing a control pressure level in a respirator for human patients which is equipped with a tracheal tube connected to the respirator and connectable to the patient's trachea with an attachment tube connected to the tracheal tube and having a cavity therein with two openings, one communicating with the end of the tracheal tube and the other communicating with a space for receiving exhaled breathing air, comprise producing an oscillating gas stream by directing at least one gas jet into the tracheal tube while the pressure and frequency are controlled so as to modulate the oscillating gas stream and thus vary the pressure level propagating it to the tracheal tube. Advantageously the operation is characterized by using two or more gas jets with at least one pair of the gas jets discharging in mutually opposite directions.

The two gas jets discharged in opposite directions can be varied virtually in any way, as far as the pressure and frequency is concerned. Experience has further shown that a great variety of modulated curves may be obtained so that an artificial underpressure also may be produced in the tracheal tube. To produce an excess pressure in the tracheal tube, the pressure and frequency dependent intensity of the gas jet in the direction of the tracheal tube is made preponderant, while the intensity of the gas jet in the opposite direction is made preponderant if an underpressure is to be produced in the tracheal tube.

The gas jets are usually produced separately, each by means of a pulse-controlled valve stage. The time of propagation of the gas pressure wave through the tracheal tube can be compensated for in a relatively simple way by directing the control pulse train of one of the gas jets through a corresponding electronic delay element.

Advantageously, the frequency of the gas jet is made adjustable within the range of 10 to 1,200 pressure pulses per minute. The working pressure is usually between 0.5 and 5 bar.

The respirator in accordance with the invention is not limited to carrying out the inventive method, it may be employed also for other therapeutic purposes, since, for example one of the gas jets may be switched off.

The inventive respirator is equipped with a tracheal tube which is connectable to the trachea and connected, by its end remote from the patient's body, to an attachment tube having a substantially cylindrical cavity with two end openings of which one communicates with the tracheal tube end and the other with a space for receiving the exhaled breathing air. The device is further equipped with a fresh gas line opening into the attachment tube and with at least one gas jet pipe opening into the cavity of the attachment tube, and at least two gas jet pipes with nozzle tips, of which one nozzle tip discharges or points substantially in the direction of the tracheal tube while the other nozzle tip discharges or points substantially in the opposite direction. To extend the application of respirators equipped with such attachment tubes and known per se, in which a single gas jet pipe is provided pointing in the direction of the trachea, the inventive respirator is designed with at least two gas jet pipes with nozzle tips, of which one discharges substantially in the direction of the tracheal tube, and the other substantially in the opposite direction. The second gas jet pipe may then be designed to open at a location outside the attachment tube, such as to directly discharge into the tracheal tube.

To allow a more accurate adjustment and enlarge the application range, the discharge direction of the gas jet pipes may be made adjustable. Further, it may be provided to adjust the pressure and/or frequency of the two gas jets separately. The pressures generally range between 0.5 and 5 bars, the frequency of the respiratory pulses between 0 and 1,200 per minute.

In order to produce a pressure releasing effect, the cavity of the attachment tube, or the tracheal tube part extending within the attachment tube, is advantageously constructed with a constricted portion in the zone where the nozzle tips of the gas jet pipes are located. With a corresponding adjacent flaring portion, a Venturi effect is obtained.

The inventive attachment tube, forming another part of the present subject matter, incorporates at least two gas jet pipes having nozzle tips pointing in opposite directions. Such an attachment may be designed as a tube connector for prior art standard tracheal tubes.

In accordance with the invention there is provided an apparatus for connecting a respirator to a tracheal tube to a person's trachea which comprises an attachment tube having a through bore defining an interior cavity with an opening at one end to atmosphere and an opening at an opposite end into which the tracheal tube extends, a connection for first breathing air extending into the tube from a side thereof and at least two gas jet pipes opening into the cavity each having a nozzle discharge with one being oriented generally toward the tracheal tube and the other being oriented substantially in an opposite direction.

A further object of the invention is to provide a method of regulating pressure level in a tracheal tube connection to a person which comprises using a pair of jet streams oriented to flow into a connection to the tracheal tube in opposite directions to control the pressure level in the respirator so as to modulate the gas stream which is directed to a patient.

A further object of the invention is to provide an apparatus for connecting a respirator through a tracheal tube which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 2:
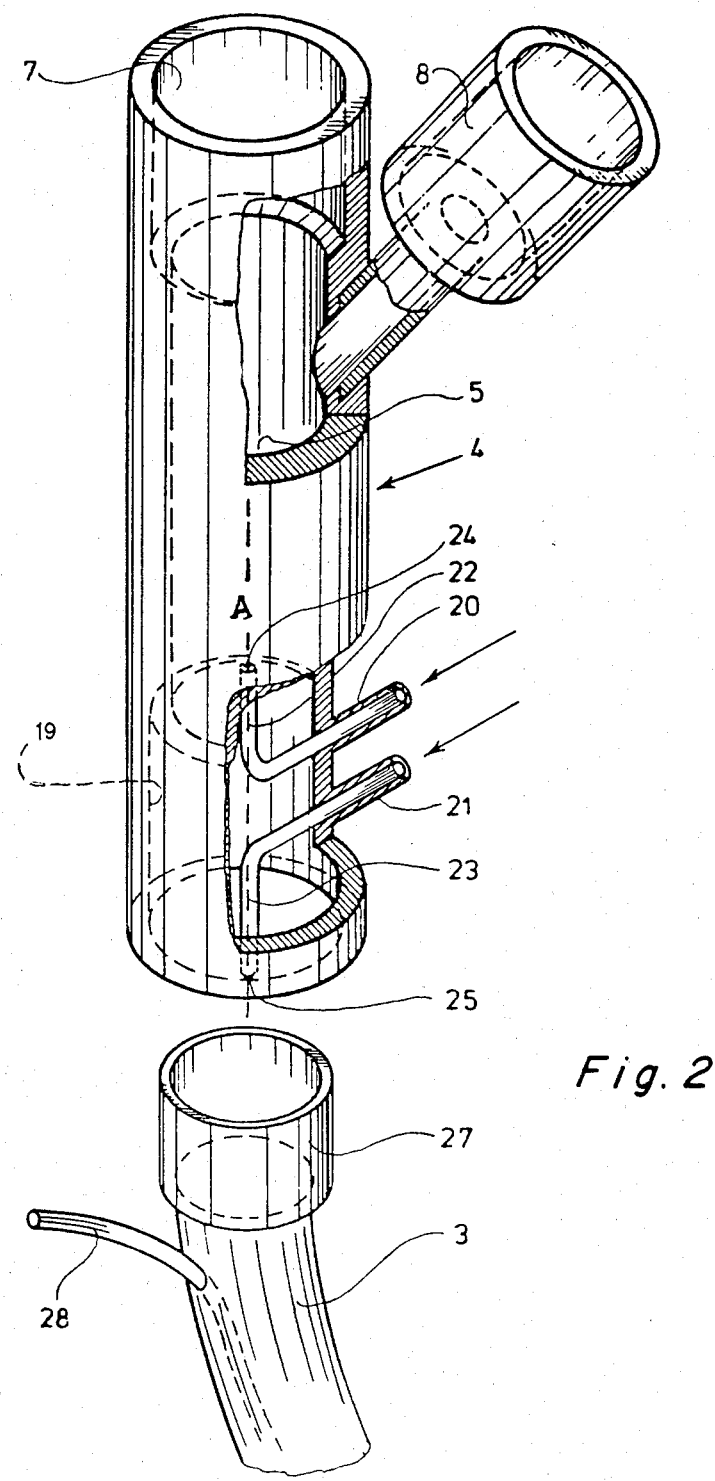
FIG. 2 is an enlarged partial perspective view indicating the attachment tube and the connection to the tracheal tube shown in FIG. 1.

Referring to the drawings in particular the invention embodied therein comprises an apparatus for connecting a respirator through a tracheal tube 3 to a person's trachea tube which comprises an attachment tube 4 having a through bore therethrough which defines an interior cavity 5. The attachment tube 4 has an opening 7 at one end to atmosphere and an opening at the opposite end into which the tracheal tube 3 extends. A connection for fresh air 8 extends into the connection tube 4 from one side thereof. In accordance with the invention at least two gas jet pipe supply lines 9 and 10 are connected to the connection tube 4. Supply lines 9 and 10 are connected respectively to a pair of gas jet pipes 20 and 21 (FIG. 2). Pipes 20 and 21 have respective discharge nozzles 24 and 25 which face in substantially opposite direction and away from each other, nozzle 25 facing into the tracheal tube 3 and nozzle 24 facing toward the center of the interior cavity 5.

Figure 1:
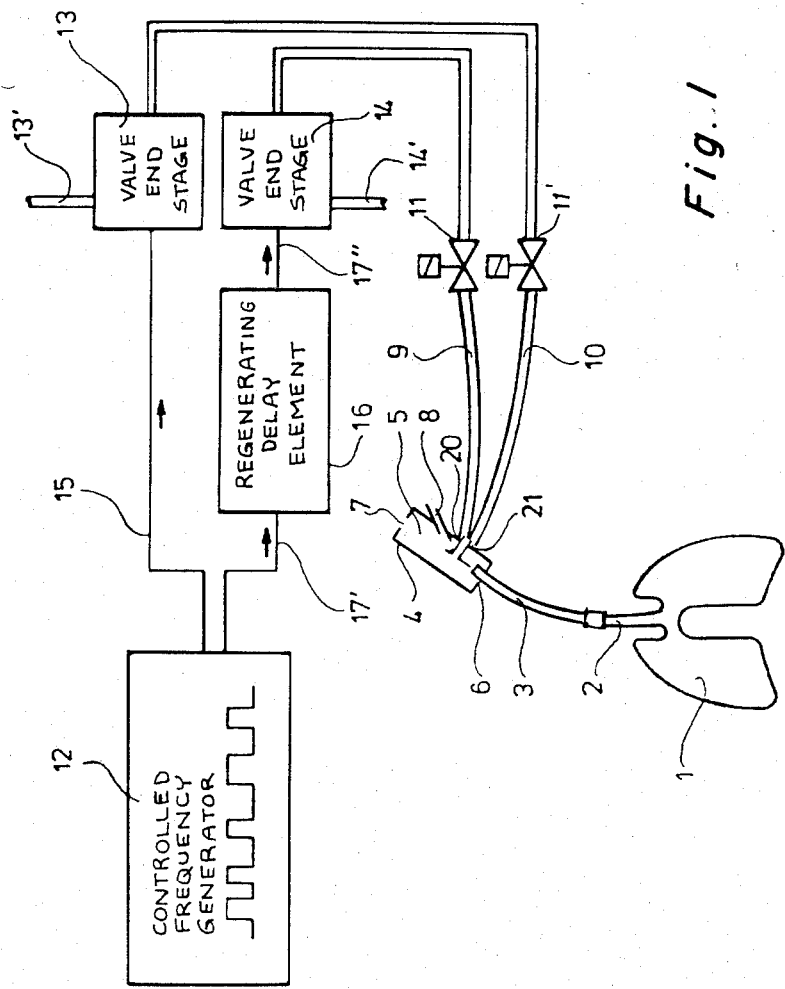
FIG. 1 is a schematic view of a respirator constructed in accordance with the invention.

FIG. 1 shows the application of the invention in a diagrammatical way, while using a block diagram. The lungs of a patient are schematically indicated at 1, and the trachea at 2. A standard tracheal tube 3 is tightly connected to trachea 2. On its end remote from the patient's body, tracheal tube 3 is connected to the attachment tube 4 having a substantial cylindrical cavity 5 with two end openings 6 and 7.

End opening 6 of attachment tube 4 is connected to tracheal tube 3, while end opening 7 permanently communicates with the atmosphere. The cross section of cylindrical cavity 5 is not constant, since an enlarged portion is provided, as explained hereinafter. From the side, fresh gas supply line 8 opens into cylindrical cavity 5 of attachment tube 4. Through line 8, breathing gas is supplied, in a manner known per se, to flow through the attachment tube under a pressure slightly exceeding (about 0.1 bar) the atmospheric pressure. Further provided are the two gas jet pipes 20 and 21 which also open into the cavity of attachment tube 4 and are designed as relatively thin hollow needles having an inside diameter of 0.9 to 1.2 mm, for example.

Gas jet pipes 20 and 21 are supplied with a gas flowing through a valve arrangement and through pressure lines 9 and 10. By means of solenoid safety valves 11, 11' which are open in de-energized state, the gas stream can in emergency instantly be shut off. Fine variations of the gas stream in the gas jet pipes are controlled through an electronic control unit including as its most important part a closed loop-controlled frequency generator 12, in turn controlling two valve end stages 13 and 14. In arrangements known per se, valve end stages 13 and 14 are supplied through gas lines 13', 14', with a gas under higher pressure generally having a composition of a breathing gas. The valve end stages then open and close in a rhythm corresponding to the wave form of pulse signals coming from frequency generator 12, so that a very rapid sequence of pressure pulses can be produced.

Valve end stages 13 and 14 operate substantially as magnetically controllable precision valves. Frequency generator 12 is controlled as to the recurrence frequency and pulse intervals, through a circuit (not shown), and valve end stage 13 is controlled directly through a first signal line 15. Second valve end stage 14 is controlled in a similar way through a line 17', 17", only a so called regenerating delay element 16 is interposed in this line. This delay element 16 is electronically controlled to delay the pulse signals supplied to second end stage 14 to an extent compensating for the time needed by the pressure wave for passing from the attachment tube through the tracheal tube to the bronchi. Due to this simple provision, an undesirable interference of signals is avoided even if complicated pulse signal curves are involved.

The two signal end stages 13 and 14 may of course be supplied with, and controlled by, different signal trains, quite independently of each other.

FIG. 2 shows an attachment tube 4 in detail, in an enlarged view. In its lowest portion 19, cylindrical cavity 5 of attachment tube 4 has its cross-sectional area enlarged by 50%. Gas jet pipes 20 and 21 protrude into cavity 5 up to a center axis A thereof where they terminate in respective axially extending end portions 22, 23 which are bent at an angle thereto. End portions 22 and 23 have nozzle tips 24, 25 at their free ends. One end portion 23 discharges or points substantially in the direction of tracheal tube 3, while the other end portion 24 discharges or points substantially in the opposite direction. By slightly turning gas jet pipes 20 and 21 about their axes extending within their walls, the directions of the jets can be varied.

To connect tracheal tube 3 to attachment tube 4, the end portion thereof has a collar 27 which is tightly engaged in the enlarged portion 19 of tube 4. Altogether, the narrowing and the gradual enlarging of the cross-sectional area of flow in cylindrical cavity 5 results in a venturi-like effect, and the gas jet pulses produce a pressure which propagates into the tracheal tube. Tests have shown that with a corresponding control of the intensity of the gas jet, mainly depending on the pressure and pulse frequency, both excess pressures and underpressures can be produced in the tracheal tube.

FIG. 2 further shows that the fresh gas supply line 8 opens into cavity 5 at an angle to cylinder axis A, with the axial vectorial component of the gas blow pointing in the direction of the tracheal tube 3. Preferably the blow-in direction forms an angle of 45° with the axis of the tracheal tube, the angle may be varied between 30° and 60°, however. Fresh gas supply line 8 may be attached in various ways, such as prependicularly to axis A or in the form of a tee connected to opening 7. What is essential is to obtain, through the cylindrical shape of cavity 5 and a relatively large clear sectional area of flow, a spontaneous breathing of the patient, and no obstruction to coughing. Further ensured must be a free draining of the attachment tube to enable the patient to get rid, without hindrance, even of larger mucous lumps which would definitely increase the breathing effort. Care is therefore taken to maintain the clear passage area remaining in cavity 5 of tube 4 after fixing gas jet pipes in place substantially equal to that of the diameter of the tracheal tube.

As may be learned from FIG. 2, tracheal tube 3 may be provided with a measuring line 28 for sensing the pressure in the bronchi.

The position of end portion 22 and 23 of the gas jet pipes, terminating with nozzle tips 24 and 25, may vary, in accordance with the specific requirements. In general, nozzle tips 24 and 25 are spaced from each other by 10 to 50 mm. They may discharge in exactly opposite directions. However, slightly different discharge directions may be provided, for example pointing more at the inner surface of cavity 5. The inner surface of cavity 5 may even be given a streamlined shape. The connection of fresh gas supply line 8 is spaced from the neighboring nozzle tip 24 of the gas jet pipe generally by a distance ensuring that the "jet effect" of gas jet pipe 20 is not undesirabley neutralized by a strong fresh gas stream. A distance of 40 to 100 mm, for example, between the respective rim of the fresh gas connection and nozzle tip 24 has proved satisfactory. Here again, what matters is to obtain a light-weight attachment tube 4 as compact as possible, to minimize disturbances which might affect the patient. It is further advisable to design the attachment tube as a tube connector for conventional, standard tracheal tubes.

Figure 3:
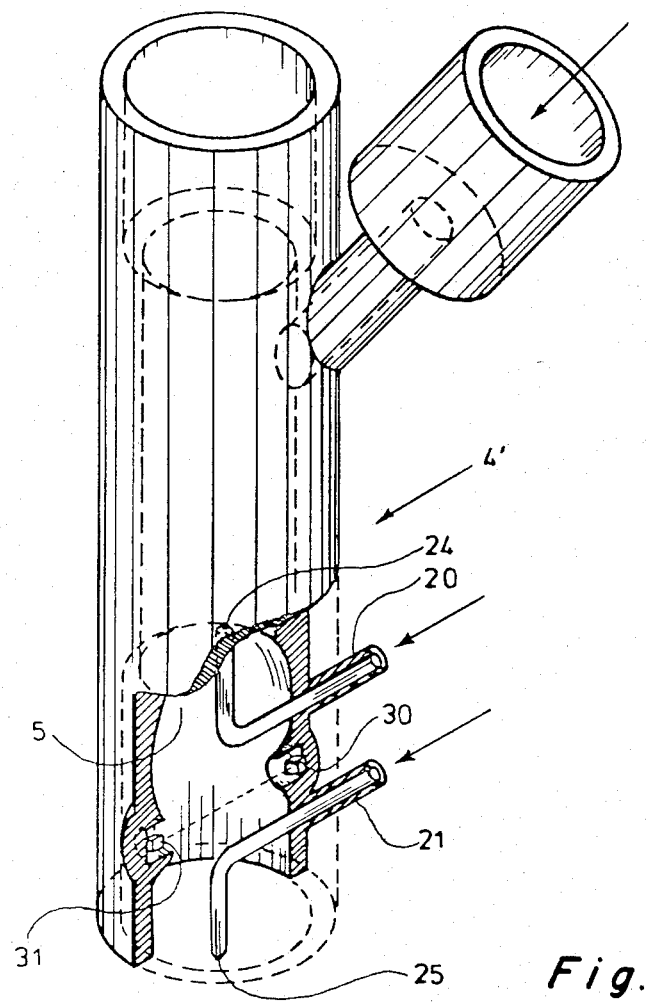
FIG. 3 is a view similar to FIG. 2 of another embodiment of the invention.

FIG. 3 shows a slightly modified embodiment of attachment tube 4' wherein the cavity 5 is enlarged in the zone of nozzle tips 24 and 25 of gas jet pipes 20 and 21, and then a little constricted, and enlarged again. This attachment tube 4' is connected to tracheal tube 3 in a way similar to that shown in FIG. 2. What is different is that the two gas jet pipes 20, 21 are introduced through the wall of attachment tube 4' with a larger axial spacing, thus at more widely spaced locations. In the space therebetween, an infrared transmitter 30 is inserted cooperating with an infrared detector or receiver provided at the opposite side. Device 30 and 31 serves the purpose of measuring the $CO_2$ content of the air present between nozzle tips 24, 25 and thus primarily the $CO_2$ content of the expired air. An inadaquate drop of this $CO_2$ content means that an insufficient amount of expired air reaches the measuring device, thus that the gas exchange is no longer satisfactory. In such a case, an alarm must be started. The breathing may be brought to a satisfactory level by intensifying the ventilation, for example. To improve the monitoring, an additional pressure sensor 30, 31 may be provided in attachment tube 4', in the zone of nozzle tipes 24, 25 (see FIG. 3), since the pressure at that location is critical for the continuous respiration of the patient.

By controlling the recurrence frequency and the pulse intervals, as well as the pressure of the gas stream, i.e. of a humidified, preferably $O_2$-enriched breathing gas, the pressure level in the tracheal tube is controlled to a substantial extent.

Figure 4:
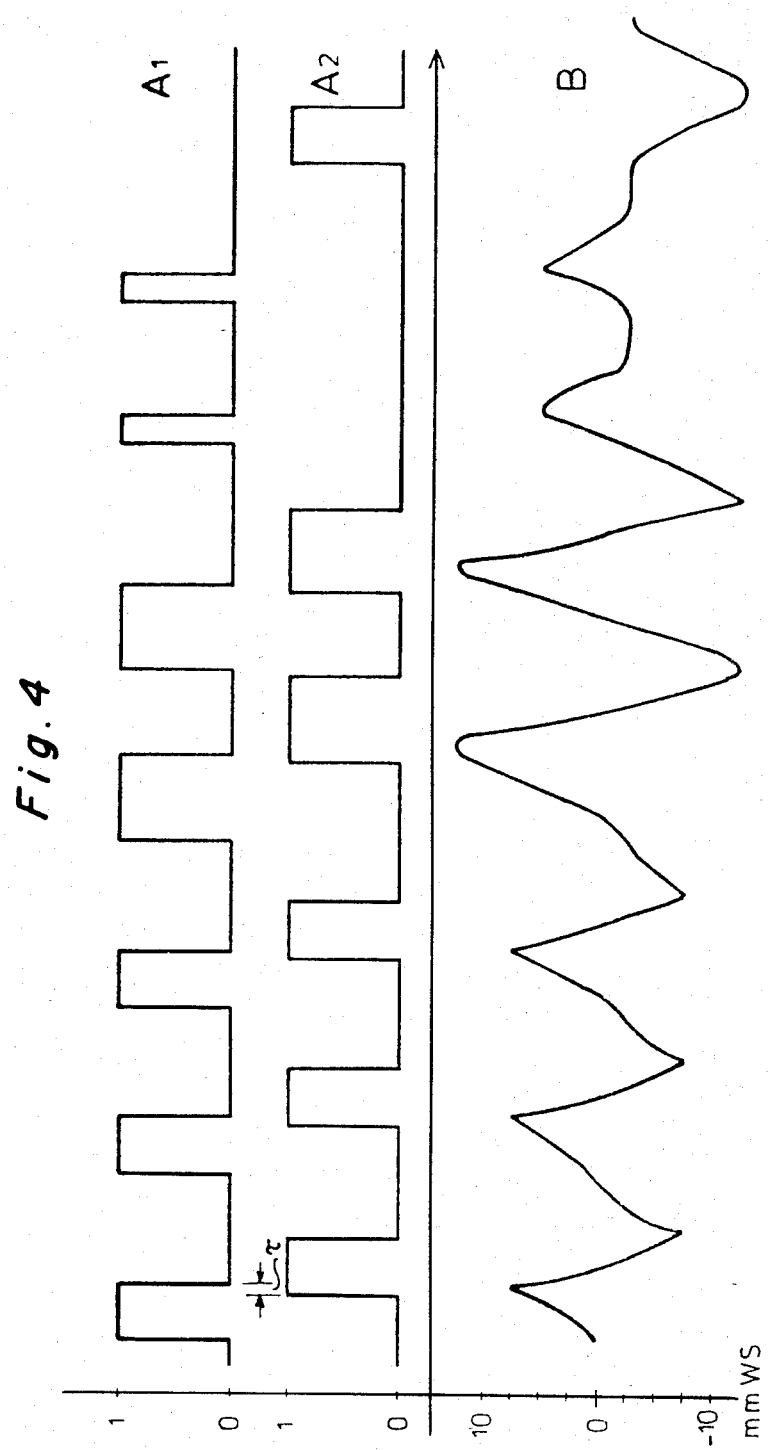
FIG. 4 is a curve representing the pressure variation obtainable in the trachea with two pulse chains directed through the valve in end stages.

FIG. 4 is a synoptic showing of three curves resulting from two control curves. More particularly curve A1 represents a pulse train delivered from frequency generator 12 to first valve stage 13;

curve A2 represents a pulse train delivered from frequency generator 12 to second valve stage 14;

curve B is the resulting pressure curve within tracheal tube 3, at the transition of the bronchi.

Figure 5:
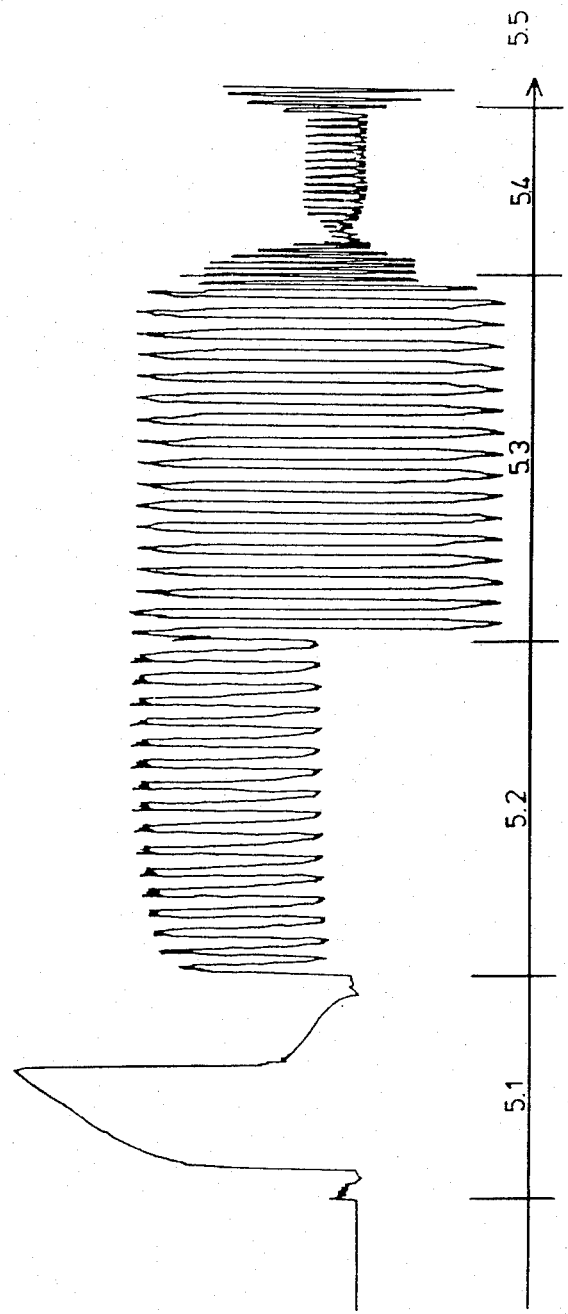
FIG. 5 shows a curve indicating examples in modulation of the basic curve.

With a high recurrence frequency, such as of 1,000 pulses per minute, the trains of pulse signals represented by curves A1 and A2 extend in every instance over more pressure surges, so that the resulting curve B is somewhat blurred (see also FIG. 5). Due to the interposition of the delay element, lower curve A2 lags by a time interval tau ($\tau$). Tau is the period of time needed by the pressure wave within the tracheal tube to pass from the mid point between nozzle tips 24, 25 to the transition to the bronchi. It is evident that the respective signal trains which can be produced in the frequency generator through a variety of control inputs, result in an exactly defined respiratory curve. In particular, the I-E ratio can be maintained accurately and exactly. By I-E ratio, the ratio of the inspiration intensity to the expiration intensity is understood. A great variety of pressure patterns can be produced with the curve being necessarily adjusted in accordance with the requirements of therapy and monitoring.

Figure 6:
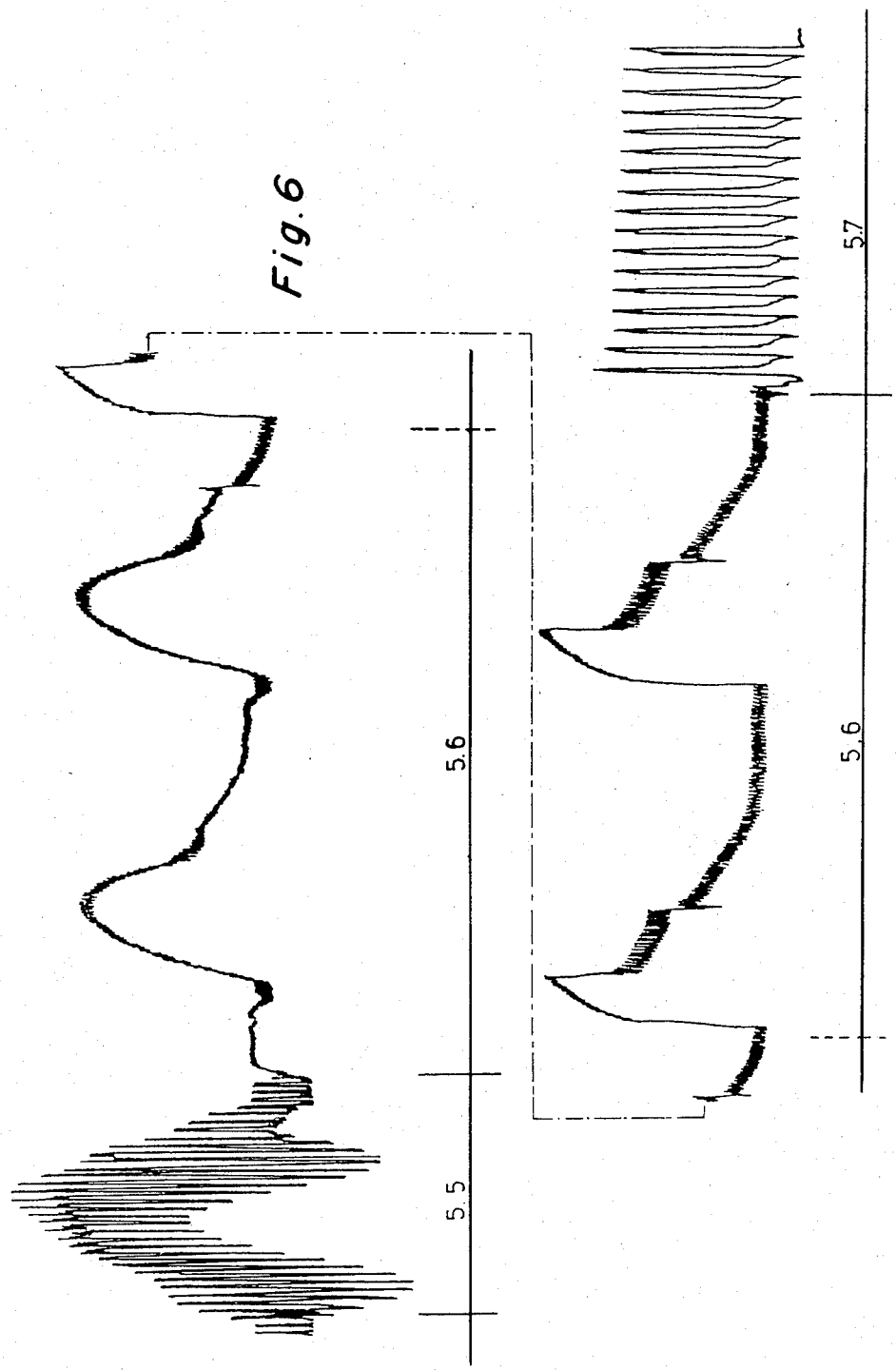
FIG. 6 shows a variation of the curve shown in FIG. 5.

FIGS. 5 and 6 show, in several sections 5.1 to 5.7, what shapes of respiratory curves may occur. This showing particularly demonstrates that also very steep pulse edges dP/dt can be produced. The curves have been obtained in tests with so called model lungs. More particularly, the curves of FIGS. 5 and 6 show the following specific patterns:

5.1 jet ventilation for resuscitation, particularly step pulse edges are needed.

5.2 high-frequency jet ventilation with a large dP/dt but a small $P_{max}$.

5.3 high frequency oscillations, where the valve end stages 13 and 14 operate aperiodically. The average respiratory pressure is 0.

5.4 mixed-mode vibration: the mucus production and coughing are stimulated.

5.5 a higher frequency is produced. The gas displacement effect within the bronchi and the tracheal tube is increased.

5.6 "imitated" Engström pressure curves are shown. These curves are preferred in an artificial respiration of patients having no damaged thorax.

5.7 a shorter pulse duration than in 5.2 is provided, thus a lower average pressure.

All the curves 5.1 to 5.7 and still other curves can be obtained without "stepping" or changing the attachment tube of the tracheal tube. The shape of the curves is varied only by varying the adjusting parameters, namely the recurrence frequency, pulse intervals, and the pulse time ratio, in the two gas jet pipes 20,21.

Altogether, the inventive method and respirator offer a surprisingly broad leeway for varying the respiration of injured patients.

While specific embodiments of the invention have been shown and described in detail to illustrate the application of the principles of the invention, it will be understood that the invention may be embodied otherwise without departing from such principles.

What is claimed is:

1. An apparatus for connecting a respirator through a tracheal tube to a person's trachea, comprising a tracheal tube adapted to be connected to the person's trachea, an attachment tube having one end connected to said tracheal tube and having a through bore defining an interior cavity, said bore having an opposite opening at one end to atmosphere and an opening at the opposite end into which the tracheal tube extends, a connection for fresh breathing air extending into said attachment tube from a side thereof, and at least two separate gas jet pipes opening into the cavity and each having a gas jet nozzle one of which is directed generally toward said tracheal tube and the other of which is directed in substantially an opposite direction, said connection for fresh breathing air including a fresh gas supply line having a rim portion interconnected with said attachment tube that is located between the opposite opening of said attachment tube and the other of said nozzles and spaced from the other of said two gas jet nozzles which is directed away from said tracheal tube by from 20 to 100 mm.

2. An apparatus according to claim 1, including pressurized gas supply means connecting said two gas jet tubes providing adjustable gas pressure pulses to said jet tubes.

3. An apparatus according to claim 1, wherein said cavity includes a narrowed area in the vicinity of the connection of said jet tubes to said cavity.

4. An apparatus according to claim 1, wherein said connection for fresh breathing air opens into said cavity.

5. An apparatus according to claim 1, wherein said connection for fresh breathing air into said attachment tube is made at a predetermined angle to the axis of said tube which is adjustable.

6. An apparatus according to claim 1, wherein said connection for fresh breathing air into said attachment tube is at an angle to the axis of the attachment tube which is between 30° and 60° and directed in a direction toward the tracheal tube.

7. An apparatus according to claim 1, wherein said at least two gas jet tubes includes a first tube having a tube portion extending substantially parallel to the axis of said attachment tube in a direction toward the end thereof opening to the atmosphere and the other of said two gas jet pipes has a pipe portion extending substantially parallel to the axis of said attachment tube with a discharge directed in the direction of the opposite opening.

8. An apparatus according to claim 1, wherein said attachment tube comprises a tube of plastic material having a diameter size of a standard form at the tracheal tube end opening thereof, and including a tracheal tube having a collar which fits into the opening at the tracheal tube end of said attachment tube.

9. An apparatus for connecting a respirator through a tracheal tube to a person's trachea, comprising a tracheal tube adapted to be connected to the person's trachea, an attachment tube having one end connected to said tracheal tube and having a through bore defining an interior cavity, said bore having an opposite opening at one end to atmosphere and an opening at the opposite end into which the tracheal tube extends, a connection for fresh breathing air extending into said attachment tube from a side thereof, and at least two separate gas jet pipes opening into the cavity and each having a nozzle discharge one of which is directed generally toward said tracheal tube and the other of which is directed in substantially an opposite direction, and a pressure sensor in said attachment tube.

10. An apparatus for connecting a respirator through a tracheal tube to a person's trachea, comprising a tracheal tube adapted to be connected to the person's trachea, an attachment tube having one end connected to said tracheal tube and having a through bore defining an interior cavity, said bore having an opposite opening at one end to atmosphere and an opening at the opposite end into which the tracheal tube extends, a connection for fresh breathing air extending into said attachment tube from a side thereof, and at least two separate gas jet pipes opening into the cavity and each having a nozzle discharge one of which is directed generally toward said tracheal tube and the other of which is directed in substantially an opposite direction, and sensor means for detecting the composition of the gas located in said attachment tube between said nozzle discharge of said two gas jet pipes, sensor means comprising a light source and a corresponding receiver aligned with said light source provided in respective opposite walls of said attachment tube.

11. A method of producing a control pressure level in a respirator for human patients which is equipped with a tracheal tube having one end connected to the respirator and an opposite end connectable to the patient's trachea, and with an attachment tube connected between the tracheal tube and respirator and having a flow passage therethrough communicating with the atmosphere for discharging exhaled air from the patient and for supplying fresh breathing air to the patient, comprising:
    directing a stream of fresh breathing air through the flow passage of the attachment tube, to the patient for respirating the patient;
    directing first gas jet pulses in a first direction through the flow passage and axially toward the tracheal tube at a selected pressure and frequency for increasing pressure in the tracheal tube;
    directing second gas jet pulses in a second direction substantially opposite to said first direction, through the flow passage and axially away from the tracheal tube at a selected pressure and the selected frequency to decrease pressure in the tracheal tube; and
    modulating the pressure in the tracheal tube by simultaneously directing the first and second gas jet pulses through the flow passage and controlling the selected pressure and frequency for the first and second gas jet pulses to modulate the pressure in the tracheal tube with the pressure increasing when the pressure and frequency of the first gas jet pulses predominate over the pressure and frequency of the second gas jet pulses, and the pressure decreasing when the pressure and frequency of the second gas jet pulses predominate over the pressure and frequency of the first gas jet pulses, the selected frequency of the gas jet pulses being within the range of 10 to 1,200 jet pulses per minute.

12. A method according to claim 12 wherein a pulse controlled valve and stage is provided for each of the gas jet pulses and wherein a control pulse train of one of the gas jet pulses is delayed relative to the second gas jet pulses in order to compensate for the time needed for the gas stream to pass through the person's trachea.

13. A method according to claim 12, wherein the tracheal tube is connected to said attachment tube which as a substantially cylindrical cavity therein forming said flow passage and including directing the fresh breathing gas into the cylindrical cavity from a side of the attachment tube while directing said first and second gas jet pulses intothe attachment tube, a discharge direction of at least one of the first and second gas jet pulses being adjustable.

14. A method according to claim 12, including directing said first and second gas jet pulses away from each other in said first and second directions.

* * * * *